(12) United States Patent
Yoo et al.

(10) Patent No.: US 10,060,885 B2
(45) Date of Patent: Aug. 28, 2018

(54) LIQUID CHROMATOGRAPHY APPARATUS FOR FAST MEASURING

(71) Applicant: WITHTECH INC, Daejeon (KR)

(72) Inventors: Seoung-Kyo Yoo, Daejeon (KR); Eung Sun Lee, Daejeon (KR); Jin Yong Lee, Daejeon (KR); Dae Hee Kim, Daejeon (KR)

(73) Assignee: WITHTECH INC, Daejeon (KR)

( * ) Notice: Subject to any disclaimer, the term of this patent is extended or adjusted under 35 U.S.C. 154(b) by 211 days.

(21) Appl. No.: 14/904,059

(22) PCT Filed: Jul. 10, 2014

(86) PCT No.: PCT/KR2014/006193
§ 371 (c)(1),
(2) Date: Jan. 8, 2016

(87) PCT Pub. No.: WO2015/005692
PCT Pub. Date: Jan. 15, 2015

(65) Prior Publication Data
US 2016/0153941 A1 Jun. 2, 2016

(30) Foreign Application Priority Data
Jul. 10, 2013 (KR) ........................ 10-2013-0080842

(51) Int. Cl.
*G01N 13/00* (2006.01)
*G01N 30/84* (2006.01)
(Continued)

(52) U.S. Cl.
CPC ............. *G01N 30/20* (2013.01); *B01D 15/14* (2013.01); *B01D 15/24* (2013.01); *B01D 15/242* (2013.01);
(Continued)

(58) Field of Classification Search
USPC .............................................. 73/61.55, 64.52
See application file for complete search history.

(56) References Cited

U.S. PATENT DOCUMENTS

| | | | | |
|---|---|---|---|---|
| 5,135,549 A | * | 8/1992 | Phillips | G01N 30/30 210/198.2 |
| 7,374,674 B2 | * | 5/2008 | Miyauchi | G01N 30/30 210/175 |
| 2011/0116973 A1 | * | 5/2011 | Choikhet | G01N 30/38 422/81 |

FOREIGN PATENT DOCUMENTS

| | | |
|---|---|---|
| JP | H05027665 U | 4/1993 |
| JP | 4372419 B2 | 11/2009 |

(Continued)

OTHER PUBLICATIONS

ISA Korean Intellectual Property Office, International Search Report Issued in Application No. PCT/KR2014/006193, dated Sep. 24, 2014, WIPO, 2 pages.

Primary Examiner — Clayton E Laballe
Assistant Examiner — Warren K Fenwick
(74) Attorney, Agent, or Firm — McCoy Russell LLP (57) ABSTRACT

Provided is a liquid chromatography apparatus for fast measuring, and more particularly, a liquid chromatography apparatus which includes a first column and a second column having different component separations for an interest component within a sample and makes components primarily separated in the first column be secondarily separated in the second column of a first channel unit before a switching valve is switched, makes the components primarily separated in the first column be continuously discharged through a second channel unit after the switching valve is switched, thereby improving the component separation and achieving the fast measuring.

8 Claims, 8 Drawing Sheets

(51) Int. Cl.
 *G01N 30/20* (2006.01)
 *G01N 30/60* (2006.01)
 *B01D 15/14* (2006.01)
 *B01D 15/24* (2006.01)
 *G01N 30/96* (2006.01)
 *G01N 30/02* (2006.01)
(52) U.S. Cl.
 CPC ......... *G01N 30/6039* (2013.01); *G01N 30/96* (2013.01); *G01N 2030/027* (2013.01)

(56) References Cited

FOREIGN PATENT DOCUMENTS

| | | |
|---|---|---|
| JP | 4980740 B2 | 7/2012 |
| JP | 5028109 B2 | 9/2012 |
| KR | 1020080059217 A | 6/2008 |

\* cited by examiner

FIG. 1

[PRIOR ART]

$(P_1 \simeq P_2 \simeq P_3, P_4 \simeq P_5 \simeq P_6)$

FIG. 8

LIQUID CHROMATOGRAPHY APPARATUS FOR FAST MEASURING

CROSS REFERENCE TO RELATED APPLICATIONS

The present application is a U.S. National Phase of International Patent Application Serial No. PCT/KR2014/006193, entitled "LIQUID CHROMATOGRAPHY APPARATUS FOR FAST MEASURING," filed on Jul. 10, 2014, which claims priority to Korean Patent Application No. 10-2013-0080842, entitled "LIQUID CHROMATOGRAPHY APPARATUS FOR FAST MEASURING," filed on Jul. 10, 2013, the entire contents of each of which are hereby incorporated by reference for all purposes.

TECHNICAL FIELD

The present invention relates to a liquid chromatography apparatus for fast measuring, and more particularly, to a liquid chromatography apparatus which includes a first column and a second column having different component separations for an interest component within a sample and makes components primarily separated in the first column be secondarily separated in the second column of a first channel unit before a switching valve is switched, makes the components primarily separated in the first column be continuously discharged through a second channel unit after the switching valve is switched, thereby improving the component separation and achieving the fast measuring.

BACKGROUND ART

Liquid chromatography is a method for separating components within a sample by interaction between a moving bed (eluent) and a fixed bed which has an advantage of simultaneously measuring several components by injecting the sample once.

However, since all the components included in the sample are discharged through a column, the liquid chromatography method requires very long time and therefore may be hardly used for fast measuring only a specific material.

Describing, for example, ion chromatography which is one kind of the liquid chromatography, the ion chromatography differently represents a detection time and separation of ions according to characteristics of the column, but the separation is generally proportional to the detection time. That is, to improve the separation, the very long detection time is required.

When the sample including all the ions such as $F^-$, $CH_3COO^-$, $Cl^-$, $NO_2^-$, $Br^-$, $NO_3^-$, and $SO_4^{2-}$ is analyzed by the ion chromatography method, in the case of the ions of F, $CH_3COO^-$, $Cl^-$, a retention time in a currently commercialized column is similar and thus the detection time is also similar, such that characteristics of resolution thereamong may deteriorate.

Further, the $SO_4^{2-}$ which is one of the materials having a very late retention time is one of the most important ions determining an analysis time.

Even though only the $F^-$ and $Cl^-$ in the samples are an analysis species of interest, when the $SO_4^{2-}$ is present, the analysis time is determined by the detection time of the $SO_4^{2-}$. The detection time of the $SO_4^{2-}$ in the sample is determined by the retention time of the column and when a subsequent sample is analyzed in the state in which the $SO_4^{2-}$ in the sample is introduced into the column and thus is not completely discharged, the $SO_4^{2-}$ affects an analysis of the subsequent sample and therefore the analysis is performed after the $SO_4^{2-}$ is completely discharged.

As one example of automation equipment, an ion chromatography analysis method used in a tele-monitoring system (TMS) for exhaust gas from a chimney is more excellent than an ion electrode method or a non-dispersive infrared method which is used in the related art, but takes a long analysis time and therefore may be hardly applied.

Since the exhaust gas from the chimney is managed by an environmental law of an effluent quality standard, a total quantity standard, and the like, performance of the TMS for exhaust gas from a chimney is legislated. One of the legislated performances of an analyzer is a response time and since in the case of the non-dispersive infrared method, the response time is 5 minutes and in the case of the ion electrode method, the response time is 10 minutes, in order for the ion chromatography to be used in the TMS, a very fast analysis of 10 minutes or so is required.

In particular, the exhaust gas from the chimney includes very various components in addition to a target material and since the components act as an intervening factor, there is a need to completely separate the components and perform the fast measuring of 10 minutes or so.

To solve the foregoing problems, the related art manually or automatically controls a kind of columns, a concentration or a composition of the moving bed, a flux of the moving bed, and the like to improve the resolution among $F^-$, $CH_3COO^-$, and $Cl^-$ having a short retention time, but delays the detection of $SO_4^{2-}$ and thus may not reduce the total analysis time.

Figure 1:
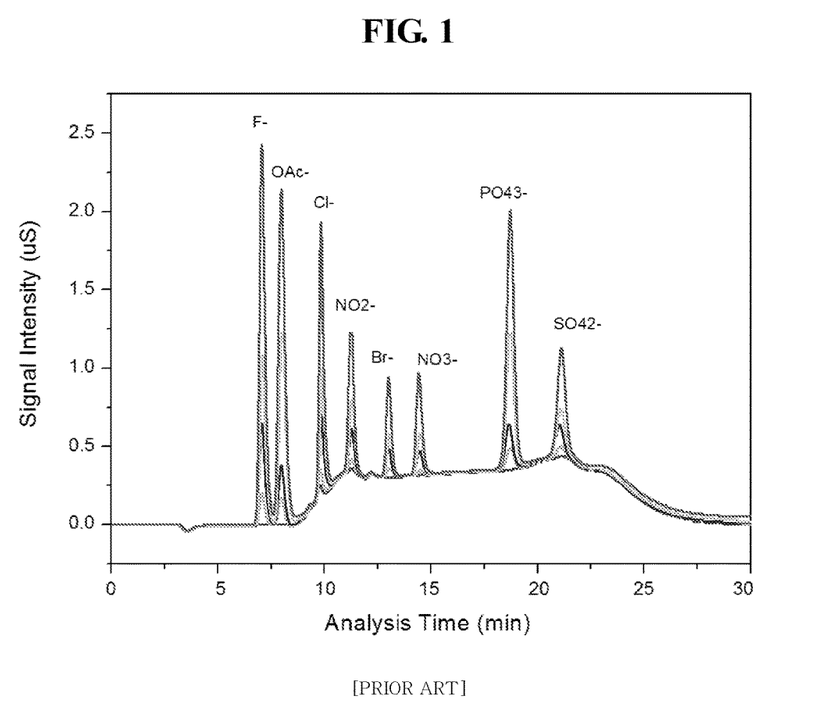
FIG. 1 is an analysis chromatogram illustrating analysis characteristics of a gradient method.

FIG. 1 illustrates that the separation is improved by controlling the concentration of the moving bed and it may be appreciated from FIG. 1 that the separation is improved, the analysis time is longer, and it takes 30 minutes or more due to a stabilization time required for subsequent analysis after the concentration of the moving bed is controlled.

As the related art, Korean Patent Application No. 2008-7009108 (filing date: Apr. 16, 2008, Title: Multidimensional Chromatography Apparatus and Method) uses a column switching method for removing a matrix from a sample but does not yet achieve reduction in an analysis time and improvement in separation.

RELATED ART DOCUMENT

Patent Document

Korean Patent Application No. 2008-7009108 (filing date: Apr. 16, 2008, Title: Multidimensional Chromatography Apparatus and Method)

DISCLOSURE

Technical Problem

An object of the present invention is to provide a liquid chromatography apparatus for fast measuring, and more particularly, to a liquid chromatography apparatus which includes a first column and a second column having different component separations for an interest component within a sample and makes components primarily separated in the first column be secondarily separated in the second column of a first channel unit before a switching valve is switched, makes the components primarily separated in the first column be continuously discharged through a second channel unit after the switching valve is switched, thereby improving the component separation and achieving the fast measuring.

Technical Solution

In one general aspect, a liquid chromatography apparatus using a liquid chromatography (LC) method including an ion chromatography, includes: an eluent storage unit 100 in which an eluent is stored; a first eluent supply pump 210 and a second eluent supply pump 220 which are connected to the eluent storage unit 100 to pump and move the eluent; a sample injection unit 300 which delivers the eluent and a sample injected into a sample loop 310 to a first column 510; a switching valve 400 which is connected to the first column 510 and the second eluent supply pump 220 through a first inlet 410 and a second inlet 420 to control passages of components analyzed in the first column 510 by a switching operation; a first channel unit 600 which is one of the passages of the components controlled by the switching valve 400 and includes a second column 610 connected to a first outlet 430 of the switching valve 400 and is introduced with components primarily separated in the first column 510 and secondarily separates the components before the switching valve 400 is switched; a second channel unit 700 which is the remaining one of the passages of the components controlled by the switching valve 400 and is connected to a second outlet 440 of the switching valve 400 and discharges the components primarily separated in the first column 510 as they are after the switching valve 400 is switched; and a pressure control module 710 which is connected to the switching valve 400 to constantly maintain pressures among the passages connected to the switching valve 400, wherein the components analyzed in the first column 510 continuously move through the passage.

The first channel unit 600 may include: a first suppressor 620 which is connected to the second column 610 to perform electrolysis of the eluent; and a first detection unit 630 which detects the components separated in the second column 610.

The pressure control module 710 may include: a first pressure control module 711 which is formed between the second eluent supply pump 220 and the second inlet 420 of the switching valve 400; and a second pressure control module 712 which is connected to the second outlet 440 of the switching valve 400.

The second channel unit 700 may include: a second suppressor 720 which is connected to the second pressure control module 712 to perform electrolysis of the eluent; and a second detection unit 730 which detects the components primarily separated in the first column 510 after the switching valve 400 is switched.

The pressure control module 710 may be a pressure regulator and an orifice.

The pressures among the passages connected to introduce the sample or the eluent into the switching valve 400 may be the same and the pressures among the passages connected to discharge the sample or the eluent from the switching valve 400 may be the same.

The switching valve 400 may rotate by a driver to mechanically change the passage.

The switching valve 400 may have a varying switching time according to an analysis target material.

Advantageous Effects

According to the exemplary embodiments of the present invention, the liquid chromatography apparatus for fast measuring includes a first column and a second column having different component separations and makes components primarily separated in the first column be secondarily separated in the second column of a first channel unit before a switching valve is switched, makes the components primarily separated in the first column be continuously discharged through a second channel unit after the switching valve is switched, thereby improving the component separation and achieving the fast measuring.

For example, when the ion chromatography which is a kind of liquid chromatography analyzes the sample including components such as F—, CH3COO—, Cl—, NO2-, Br—, NO3-, and SO42-, even though the SO42- having very late retention time and only the F— among the F—, the CH3COO—, and the F— having relatively earlier retention time is the analysis species of interest, the SO42- is completely discharged and then needs to be analyzed, such that there is a problem in that the analysis time is long.

To solve the above problem, according to the exemplary embodiments of the present invention, the switching valve is switched at a specific time by combining the advantages of the first column which may perform the fast analysis of the SO42- but may not separate the F— from the CH3COO— and the advantages of the second column which may maintain the separation of the F— from the CH3COO— to some degree but takes a long measurement time for the SO42- to introduce the components just before the switching into the first channel unit so as to re-separate the components in the second column and pass the components after the switching through the suppressor as they are so as to make the detector measure the components, thereby maintaining the analysis time of the characteristics of the first column.

Therefore, according to the exemplary embodiments of the present invention, the total of analysis time is required by the analysis time of the first column which may fast detect the SO42- having a very late retention time, thereby more reducing the total of analysis time than the related art and improving the separation of the components according to the characteristics of the second column.

Further, according to the exemplary embodiments of the present invention, even though the passages through which the sample or the moving bed moves are switched by the switching valve, the liquid chromatography apparatus includes the pressure control module which controls the pressures among the passages applied to the switching valve to be equal to each other and controls the pressures among the discharged passages to be equal to each other to make the fluid stably flow at the time of changing the passages among the channels, thereby securing the measurement stability.

Further, as described above, according to the exemplary embodiments of the present invention, the liquid chromatography apparatus which performs the fast measurement and is applied to the tele-monitoring system (TMS) for exhaust gas from a chimney including various components may simultaneously detect various components and thus may more improve the analysis performance than the ion electrode method or the non-dispersive infrared method which has been often used in the existing TMS.

DESCRIPTION OF DRAWINGS

The above and other objects, features and advantages of the present invention will become apparent from the following description of preferred embodiments given in conjunction with the accompanying drawings, in which.

BEST MODE

Hereinafter, a liquid chromatography apparatus for fast measuring according to an exemplary embodiment of the present invention will be described in detail with reference to the accompanying drawings.

A liquid chromatography apparatus 1 according to an exemplary embodiment of the present invention which reduces an analysis time using column switching and improves separation is configured to largely include an eluent storage unit 100, a first eluent supply pump 210, a second eluent supply pump 220, a sample injection unit 300, and a switching valve 400.

In this configuration, the liquid chromatography apparatus may be an apparatus to which a liquid chromatography (LC) or an ion chromatography method which is one field of the LC is applied.

The eluent storage unit 100 stores an eluent which is used in the liquid chromatography. The first eluent supply pump 210 and the second eluent supply pump 220 are connected to the eluent storage unit 100 to pump and move the eluent.

The sample injection unit 300 may automatically and manually deliver the eluent and a sample which is injected into a sample loop 310 to a first column 510.

The switching valve 400 is connected to the first column 510 through a first inlet 410 and is connected to the second eluent supply pump 220 through a second inlet 420 and controls passages of components which are analyzed in the first column 510 by a switching operation.

That is, in the liquid chromatography apparatus 1 according to the exemplary embodiment of the present invention, the passages of the components before the switching of the switching valve 400 and after the switching of the switching valve 400 are different from each other but the components analyzed in the first column 510 continuously move through the passages.

Figure 2:
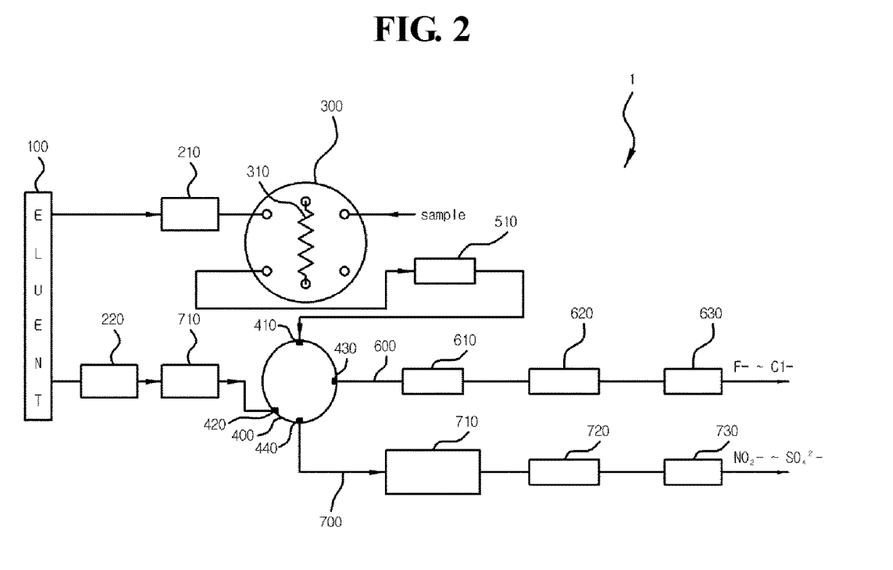
FIG. 2 is a configuration diagram of a liquid chromatography apparatus according to an exemplary embodiment of the present invention.

As illustrated in FIG. 2, the liquid chromatography apparatus 1 according to the exemplary embodiment of the present invention may be configured to include a first channel unit 600 and a second channel unit 700, in which the first channel unit 600 and the second channel unit 700 are the same as the foregoing passages, and the components before the switching of the switching value 400 move through the first channel unit 600 and the components after the switching of the switching valve 400 move through the second channel unit 700.

The first channel unit 600 is connected to a first outlet 430 of the switching valve 400 and is introduced with components primarily separated in the first column 510 before the switching of the switching valve 400 to secondarily separate the components.

To this end, the first channel unit 600 is connected to the first outlet 430 of the switching valve 400 and may be configured to include a second column 610 which is introduced with the components primarily separated in the first column 510 before the switching of the switching valve 400 and secondarily separates the components.

Further, the first channel unit 600 is connected to the second column 610 and may be configured to include a first suppressor 620 in which an electrolysis of the eluent is performed and a first detection unit 630 which detects the components separated in the second column 610.

The second channel unit 700 is connected to a second outlet 440 of the switching valve 400 and discharges the components primarily separated in the first column 510 after the switching of the switching valve 400 as they are.

In other words, the liquid chromatography apparatus 1 according to the exemplary embodiment of the present invention delivers the components analyzed in the first column 510 to the second column 610 before the switching of the switching valve 400 and re-separates the components in the second column 610 and then measures the components by the first suppressor 620 and the first detection unit 630.

After the switching valve 400 is switched, the components analyzed in the first column 510 are delivered to the second channel unit 700, the eluent is supplied to the second channel unit 700 by the operation of the second eluent supply pump 220, and the components delivered to the second channel unit 700 are analyzed and measured according to characteristics of the first column 510.

The second channel unit 700 is connected to the second outlet 440 of the switching valve 400 to analyze the components separated in the first column 510 and may be configured to include a second suppressor 720 in which the electrolysis of the eluent is performed and a second detection unit 730 which detects the components primarily separated in the first column 510 after the switching of the switching valve 400.

The first column 510 and the second column 610 may be a column which has the same characteristics but different component separations. When the characteristics are the same, the separation may be increased by controlling a concentration of the eluent, using a flux of a pump, or the like.

Describing the column having different characteristics by way of example, when an ion chromatography which is a kind of liquid chromatography analyzes a sample including ions such as $F^-$, $CH_3COO^-$, $Cl^-$, $NO_2^-$, $Br^-$, $NO_3^-$, and $SO_4^{2-}$, even though the $SO_4^{2-}$ having very late retention time and only the $F^-$ among the $F^-$, the $CH_3COO^-$, and the $F^-$ having relatively earlier retention time are an analysis species of interest, the $SO_4^{2-}$ is completely discharged and then needs to be analyzed, such that there is a problem in that an analysis time is long.

Figure 3:
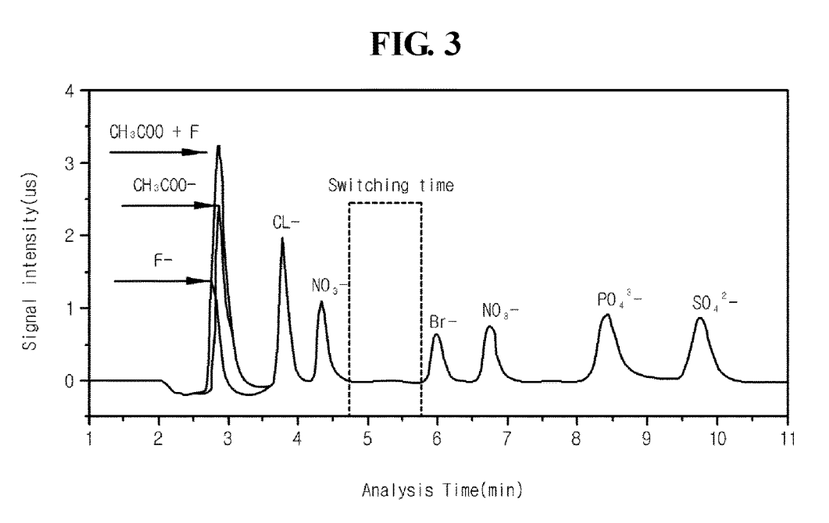
FIG. 3 is an analysis chromatogram illustrating analysis characteristics of a first column.

To solve the above problem, the liquid chromatography apparatus according to the exemplary embodiment of the present invention uses the first column 510 and the second column 610 having different component separations and improves the separation and reduces the measurement time using a column switching method. Describing in more detail, as illustrated in FIG. 3, the first column 510 may perform fast analysis on the $SO_4^{2-}$ but may not separate the $F^-$ from the $CH_3COO^-$ and thus may not accurately measure the $F^-$ which is a material to be measured.

Figure 4:
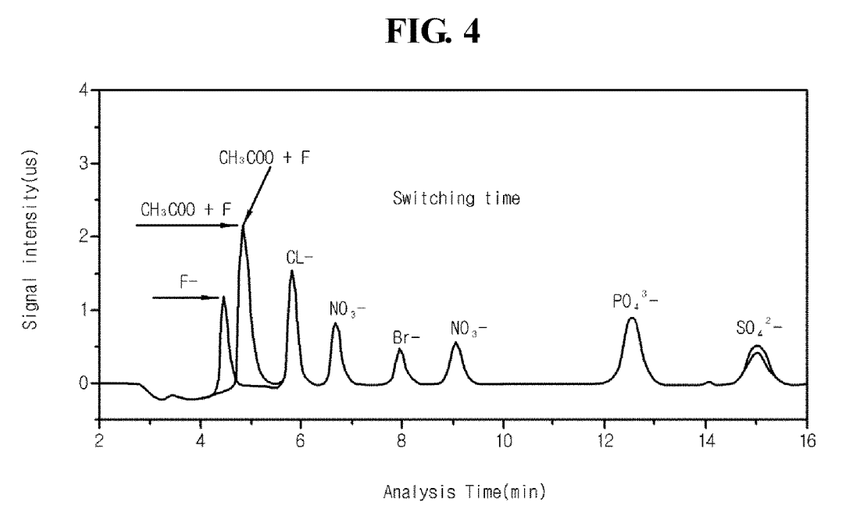
FIG. 4 is an analysis chromatogram illustrating analysis characteristics of a second column.
Figure 5:
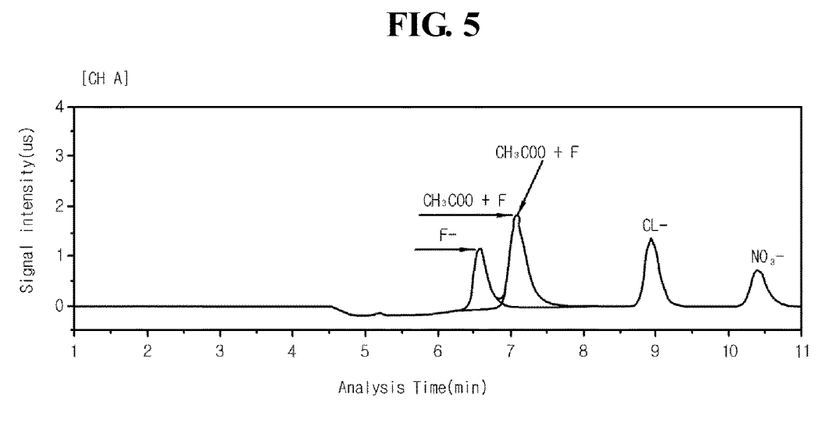
FIG. 5 is an analysis chromatogram illustrating analysis characteristics of a first channel unit.
Figure 6:
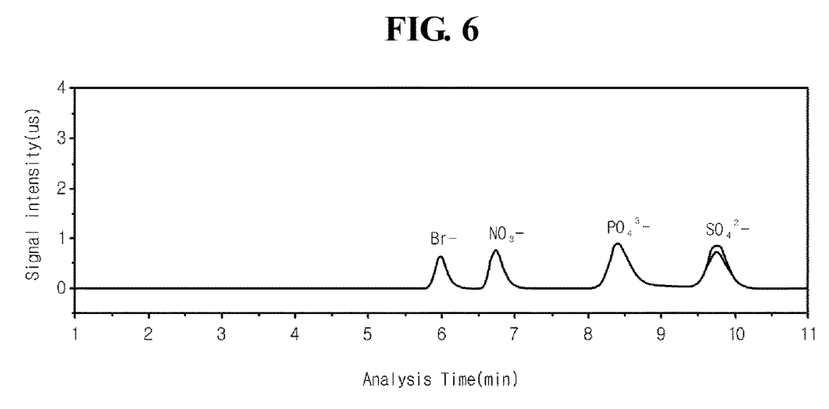
FIG. 6 is an analysis chromatogram illustrating analysis characteristics of a second channel unit.

On the other hand, as illustrated in FIG. 4, the second column 610 has a characteristic which maintains the separation of the F— from the CH3COO— to some degree but takes a long measurement time for the SO42-.

Therefore, the liquid chromatography apparatus 1 according to the exemplary embodiments of the present invention switches the switching valve 400 at a specific time by combining the advantages of the first column 510 which may perform the fast analysis on the SO42- but may not separate the F— from the CH3COO— and the advantages of the second column 610 which may maintain the separation of the F— and the CH3COO— to some degree but takes a long measurement time for the SO42- to introduce the components just before the switching into the first channel unit 600 so as to re-separate the components in the second column 610 and pass the components after the switching through the suppressor as they are so as to make the detector measure the components, thereby maintaining the analysis time of the characteristics of the first column 510.

In other words, the liquid chromatography apparatus 1 according to the exemplary embodiment of the present invention delivers the components separated in the first column 510 to the second column 610 of the first channel unit 600 before the switching of the switching valve 400 to make the F— and the CH3COO— which are not properly separated in the first column 510 be re-separated in the second column 610 and switches the switching valve 400 at a certain moment to introduce the components after the detection of the F— and the CH3COO— into the second channel unit 700, thereby making the second suppressor 720 and the second detection unit 730 fast measure the SO42-.

Therefore, according to the exemplary embodiments of the present invention, a total of analysis time is required by the analysis time of the first column 510 which may fast detect the SO42- having a very late retention time, thereby more reducing the total of analysis time than the related art and improving the separation of the components according to the characteristics of the second column 610.

Figure 8:
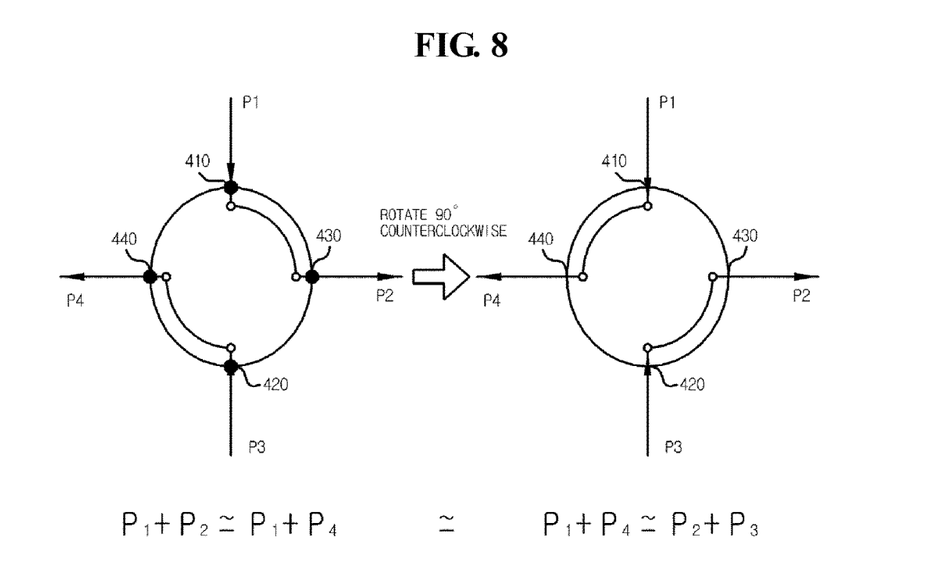
FIG. 8 is a conceptual diagram illustrating an operation state of a switching value in a liquid chromatography apparatus according to the exemplary embodiment of the present invention.

In this case, the switching valve 400 rotates by a driver such as a motor and thus may be formed to mechanically change the passage. As illustrated in FIG. 8, the switching valve 400 may be configured to include a first path 401 which connects the first column 510 to the first channel unit 600 and a second path 402 which connects the second eluent supply pump 220 to the second channel unit 700, and rotates 90° counterclockwise so that the sample passing through the first column 510 may be delivered to the second column 610 of the second channel unit 700 to make the first path 401 connect between the first column 510 and the second channel unit 700.

Therefore, the switching valve 400 may disconnect between the first channel unit 600 and the second channel unit 700 to prevent a solution from remaining, thereby preventing inter-channel interference.

The existing gas chromatography apparatus uses a method for controlling a pressure of a passage to change a detection channel of an analysis target material; however, the exemplary embodiment of the present invention is applied to a liquid chromatography in which a moving bed is a solution, in which since the solution has viscosity unlike gas, it is substantially impossible to change a delivery direction of a sample by controlling a pressure of a passage and when a method for changing a channel by a pressure is applied, if one side is not completely sealed, the inter-channel interference occurs due to the phenomenon that a liquid also remains in the other side due to a capillary phenomenon and viscosity and therefore the method for changing a channel by a pressure is not suitable.

Therefore, the exemplary embodiment of the present invention mechanically changes the passage using the switching valve 400.

Further, according to the exemplary embodiment of the present invention, the sample passes through the first column and then is continuously pushed by a pump in front stage of the first column and the second column is used as soon as the sample passes through the switching valve, such that the analysis time is minimized and a dead vol. of the passage is minimized to prevent peaks from spreading and make the peaks sharp, thereby maintaining the resolution between the peaks.

In this case, in transmitting the eluent and the sample using the pump, the pressure among all the channels is maintained the same to form a stable flow of fluid at the time of changing the passages among the channels. In particular, in the liquid chromatography apparatus 1 according to the exemplary embodiment of the present invention, the passage is changed from the switching valve 400 as a starting point and to constantly maintain a flux of the pump supplying the eluent, the pressure of all the portions of a front stage of the switching valve 400 into which the eluent is introduced is maintained the same and the pressure of the passage of a back stage of the switching valve 400 is maintained the same to prevent the change in pressure at the time of switching the valve, thereby securing the measurement stability.

To this end, the liquid chromatography apparatus 1 according to the exemplary embodiment of the present invention may be configured to further include a pressure control module 710 which is connected to the switching valve 400 to constantly maintain the pressures among the passages connected to the switching valve 400.

In this case, the pressure control module 710 may be configured to include a first pressure control module 711 which is disposed between the second eluent supply pump 220 and a second inlet 420 of the switching valve 400 and a second pressure control module 712 which is disposed between a second outlet 440 of the switching valve 400 and the second suppressor 720.

The switching valve 400 may be variously configured using multi ports of four ports or more, but in this case, the overall pressure of the portion in which the eluent flows may be maintained the same.

In the liquid chromatography apparatus 1 according to the exemplary embodiment of the present invention, most pressure is generated by the first column 510 and the second column 610 and in this case, the generated pressure becomes a high pressure as several hundreds of psi.

In the liquid chromatography apparatus 1 according to the exemplary embodiment of the present invention, when the first eluent supply pump 210 and the second eluent supply pump 220 are operated in a high pressure state and then the pressure instantly falls or rises by the switching operation of the switching valve 400, the first suppressor 620 and the second suppressor 720 may be easily damaged and since it takes long time to stabilize a set flux, the pressure needs to be constantly maintained even by the switching operation of the switching valve 400.

That is, the liquid chromatography apparatus 1 according to the exemplary embodiment of the present invention constantly maintains the pressure of the passage through which the eluent flows for stable measurement regardless of the switching direction, in which the pressure may be 500 psi or less.

Therefore, the liquid chromatography apparatus 1 according to the exemplary embodiment of the present invention is configured to include the pressure control module 710 and the pressure control module 710 is provided with a fluid inlet and a fluid outlet into and from which the fluid is introduced and discharged to generate the pressure when the fluid passes.

The pressure control module 710 may be a pressure regulator or an orifice but may be changed to others without limitation.

Meanwhile, the switching valve 400 changes the switching time according to the analysis target material for the purpose of analysis.

For example, if the retention time of the analysis target material component in the first column 510 is set to be about 5 minutes, the switching valve 400 may be switched at the elapsing time of about 6 minutes and if the retention time of the analysis target material component in the first column 510 is set to be about 3 minutes, the switching valve 400 may be switched at the elapsing time of about 4 minutes.

Figure 7:
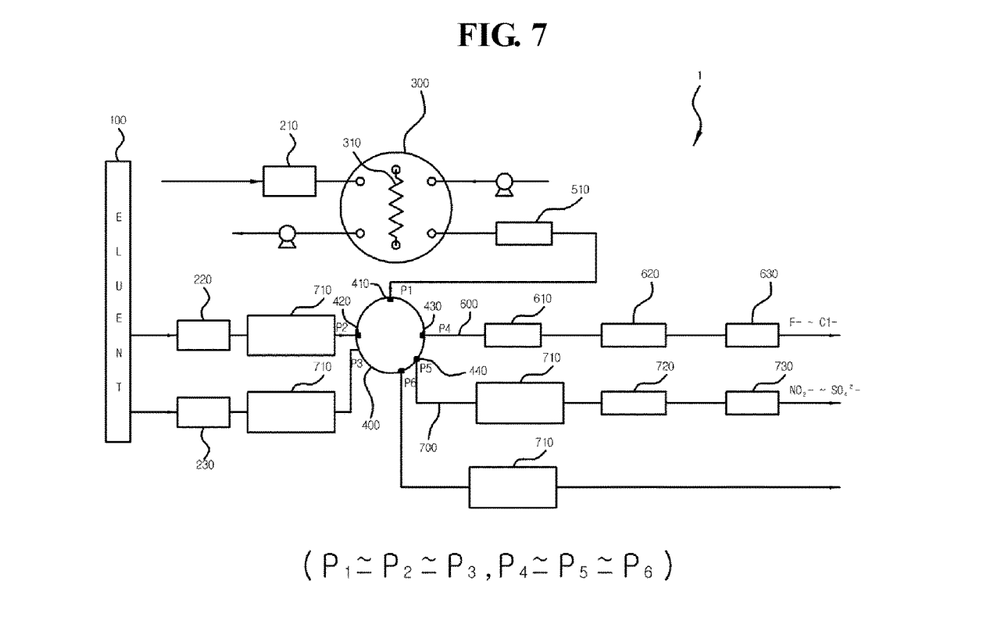
FIG. 7 is a configuration diagram illustrating a liquid chromatography apparatus according to another exemplary embodiment of the present invention.

A liquid chromatography apparatus according to another exemplary embodiment of the present invention may be configured to further include a third eluent supply pump 230 as illustrated in FIG. 7. In this case, the pressure control module 710 is disposed in an added drain line to prevent a pressure from instantly falling due to the switching operation of the switching valve 400.

Meanwhile, in the case of a clean room used to manufacture a semiconductor or a display, materials such as HF and Hcl are directly connected with process badness and therefore management of a concentration of a pollutant is very important. In other words, by accurately and rapidly measuring a concentration of HF and Hcl, rapid coping may be performed when the pollutant is generated exceeding a management concentration.

Even in the clean room, the tele-monitoring system for exhaust gas from a chimney, and an atmospheric environment monitoring system, the accurate and fast measurement technology is very important.

In particular, to apply the liquid chromatography method to the tele-monitoring system (TMS) for exhaust gas from a chimney, the liquid chromatography method needs to meet a legal standard and needs to have more excellent performance than the non-dispersive infrared method or the ion electrode method which is the measurement technology of the related art.

As described above, the liquid chromatography apparatus 1 according to the exemplary embodiments of the present invention may perform the fast measurement and thus may bapplied to the tele-monitoring system (TMS) for exhaust gas from a chimney including various components and the liquid chromatography method may simultaneously detect various components and thus may more improve the analysis performance than the ion electrode method or the non-dispersive infrared method which has been often used in the existing TMS. That is, the measurement method using the liquid chromatography apparatus 1 according to the exemplary embodiment of the present invention may improve the ion separation and perform the fast measurement, and therefore may be applied to the clean room, the TMS for exhaust gas from a chimney, and the atmospheric environment monitoring system.

The present invention is not limited to the above-mentioned exemplary embodiments but may be variously applied, and may be variously modified by those skilled in the art to which the present invention pertains without departing from the gist of the present invention claimed in the claims.

(Detailed Description of Main Elements)

1: LIQUID CHROMATOGRAPHY APPARATUS
100: ELUENT STORAGE UNIT
210: FIRST ELUENT SUPPLY PUMP
220: SECOND ELUENT SUPPLY PUMP
230: THIRD ELUENT SUPPLY PUMP
300: SAMPLE INJECTION UNIT   310: SAMPLE LOOP
400: SWITCHING VALVE
401: FIRST PATH              402: SECOND PATH
410: FIRST INLET             420: SECOND INLET
430: FIRST OUTLET            440: SECOND OUTLET
510: FIRST COLUMN
600: FIRST CHANNEL UNIT
610: SECOND COLUMN
620: FIRST SUPPRESSOR
630: FIRST DETECTION UNIT
700: SECOND CHANNEL UNIT
710: PRESSURE CONTROL MODULE
711: FIRST PRESSURE CONTROL MODULE
712: SECOND PRESSURE CONTROL MODULE
720: SECOND SUPPRESSOR
730: SECOND DETECTION UNIT

The invention claimed is:

1. A liquid chromatography apparatus using a liquid chromatography (LC) method including an ion chromatography, comprising:
an eluent storage unit in which an eluent is stored;
a first eluent supply pump and a second eluent supply pump which are connected to the eluent storage unit to pump and move the eluent;
a sample injection unit which delivers the eluent and a sample injected into a sample loop to a first column;
a switching valve which is connected to the first column and the second eluent supply pump through a first inlet and a second inlet to control passages of components separated in the first column by a switching operation;
a first channel unit which is one of the passages of the components controlled by the switching valve and includes a second column connected to a first outlet of the switching valve and is introduced with components primarily separated in the first column and secondarily separates the components before the switching valve is switched;
a second channel unit which is the remaining one of the passages of the components controlled by the switching valve and is connected to a second outlet of the switching valve and discharges the components primarily separated in the first column as they are after the switching valve is switched; and
a pressure control module which is connected to the switching valve to constantly maintain pressures among the passages connected to the switching valve,
wherein the components analyzed in the first column continuously move through the passage.

2. The liquid chromatography apparatus of claim 1, wherein the first channel unit includes:
a first suppressor which is connected to the second column to perform electrolysis of the eluent; and
a first detection unit which detects the components separated in the second column.

3. The liquid chromatography apparatus of claim 1, wherein the pressure control module includes:

a first pressure control module which is formed between the second eluent supply pump and the second inlet of the switching valve; and a second pressure control module which is connected to the second outlet of the switching valve.

4. The liquid chromatography apparatus of claim 3, wherein the second channel unit includes:

a second suppressor which is connected to the second pressure control module to perform electrolysis of the eluent; and a second detection unit which detects the components primarily separated in the first column after the switching valve is switched.

5. The liquid chromatography apparatus of claim 1, wherein the first channel unit and the second channel unit are maintained at the same pressure and the pressure is equal to or less than 500 psi.

6. The liquid chromatography apparatus of claim 1, wherein the pressures among the passages connected to introduce the sample or the eluent into the switching valve are the same and the pressures among the passages connected to discharge the sample or the eluent from the switching valve are the same.

7. The liquid chromatography apparatus of claim 6, wherein the switching valve rotates by a driver to mechanically change the passage.

8. The liquid chromatography apparatus of claim 7, wherein the switching valve has a varying switching time according to an analysis target material.

* * * * *